(12) United States Patent
Ferrera et al.

(10) Patent No.: US 8,932,991 B2
(45) Date of Patent: Jan. 13, 2015

(54) PLANAR SUPPORT HAVING AN ULTRAFLAT SURFACE AND A DEVICE FOR DETECTING ANTIGENS COMPRISING SAID PLANAR SUPPORT

(75) Inventors: Francesca Ferrera, Genoa (IT); Vincenzo Ierardi, Pisa (IT); Gilberto Filaci, Genoa (IT); Enrico Millo, Genoa (IT); Gianluca Damonte, Arenzano (IT); Francesco Indiveri, Genoa (IT); Ugo Valbusa, Genoa (IT)

(73) Assignee: Universita' Degli Studi de Genova, Genoa (IT)

( * ) Notice: Subject to any disclaimer, the term of this patent is extended or adjusted under 35 U.S.C. 154(b) by 0 days.

(21) Appl. No.: 13/808,239

(22) PCT Filed: Jul. 4, 2011

(86) PCT No.: PCT/IB2011/052941
§ 371 (c)(1),
(2), (4) Date: Jan. 3, 2013

(87) PCT Pub. No.: WO2012/004721
PCT Pub. Date: Jan. 12, 2012

(65) Prior Publication Data
US 2013/0109591 A1    May 2, 2013

(30) Foreign Application Priority Data
Jul. 5, 2010   (IT) .............................. TO2010A0577

(51) Int. Cl.
*G01N 33/68* (2006.01)
*G01N 33/543* (2006.01)
*G01N 33/552* (2006.01)

(52) U.S. Cl.
CPC ...... *G01N 33/6803* (2013.01); *G01N 33/54353* (2013.01); *G01N 33/552* (2013.01)
USPC .......................................................... 506/9

(58) Field of Classification Search
CPC ........................... G01N 33/6308; G01N 33/63
USPC .......................................................... 506/9
See application file for complete search history.

(56) References Cited

U.S. PATENT DOCUMENTS

| 7,052,846 | B2 * | 5/2006 | Van Ness et al. ............ 435/6.12 |
| 2004/0058059 | A1 | 3/2004 | Linford et al. |
| 2005/0053918 | A1 * | 3/2005 | Barnea et al. .................... 435/5 |
| 2010/0029573 | A1 | 2/2010 | Weinschenk et al. |

FOREIGN PATENT DOCUMENTS

| WO | WO 99/61653 A2 | 12/1999 |
| WO | WO 2006/002141 A2 | 1/2006 |
| WO | WO 2009/066275 A1 | 5/2009 |
| WO | WO 2010/022512 A1 | 3/2010 |

OTHER PUBLICATIONS

Kaufmann et al., Review, Stamps, Inks and Substrates: Polymers in Microcontact Printing, Polymer Chemistry, 2010, 1, 371-387.*
Jung et al., Controlled Antibody Immobilization onto Immunoanalytical Platforms by Synthetic Peptide, 2008, 374, 99-105.*
Yang, H., Dissertation, Fc-Binding Hexamer Peptide Ligands for Immunoglobulin Purification, North Carolina State University, 2008, 1-233.*
Palzkill, T., Proteomics, Baylor College of Medicine, Kluwer Academic Publishers, 2005, 1-127.*
Huang et al., Protein Detection Technique by Using Surface Plasmon Resonance (SPR) with Rolling Circle Amplification (RCA) and Nanogold Modified Tags, 2007, 22, 980-985.*
Lee et al., Protein Nanoarrays Generated by Dip-Pen Nanolithography, Science, 2002, 295, 1702-1705.*
International Search Report for corresponding International Patent Application No. PCT/IB2011/052941 mailed Sep. 12, 2011.
Nettikadan, S. et al. "Detection and Quantification of Protein Biomarkers from Fewer than 10 Cells", Molecular & Cellular Proteomics, 5:895-901, 2006.
Lee, KB et al. "Protein Nanoarrays Generated by Dip-Pen Nanolithography", Science, 295: 1702-1705, 2002.
Sekula, S. et al. "Multiplexed Lipid Dip-Pen Nanolithography on Subcellular Scales for the Templating of Functional Proteins and Cell Culture", Small: 4(8): 1785-1793, 2008.
Zhang, G. et al. "Production of Nanopatterns by a Combination of Electron Beam Lithography and a Self-Assembled Monolayer for an Antibody Nanoarray", Journal of Nanoscience and Nanotechnology, 7: 410-417, 2007.
Wingren, C. et al. "Progress in miniaturization of protein arrays—a step closer to high-density nanoarrays", Drug Discovery Today, 12(19/20): 813-819, 2007.
Steinhauer, C. et al. "Improved affinity coupling for antibody microarrays: Engineering of double-$(His)_6$-tagged single framework recombinant antibody fragments", Proteomics, 6:4227-4234, 206, 2006.
Torrance, L. et al. "Oriented immobilization of engineered single-chain antibodies to develop biosensors for virus detection", Journal of Virological Methods, 134: 164-170, 2006.
Vallina-Garcia, R. et al. "Oriented immobilization of anti-pneumolysin Fab through a histidine tag for electrochemical immunosensors", Biosensors & Bioelectronics, 23: 210-217, 2007.

* cited by examiner

*Primary Examiner* — Maria Leavitt
*Assistant Examiner* — Amy M Bunker
(74) *Attorney, Agent, or Firm* — Merchant & Gould P.C.

(57) ABSTRACT

A nanoarray or microarray of antibodies includes a planar surface having an ultraflat surface, which has a planar substrate functionalized with a first monolayer of linking molecules, preferably APTES molecules, and a second monolayer of small peptides of the general formula (I) capable of binding the Fc region of antibodies. The nanoarray or microarray includes capture antibodies immobilized on the planar support, preferably in the form of a matrix of spots, and is suitable to be used for detecting antigens in a biological sample by AFM imaging.

$$Z-HN-R^1-R^2-R^3-R^4-R^5-R^6-NH-X-CO-G-COOH.$$

7 Claims, 3 Drawing Sheets

PLANAR SUPPORT HAVING AN ULTRAFLAT SURFACE AND A DEVICE FOR DETECTING ANTIGENS COMPRISING SAID PLANAR SUPPORT

This application is a National Stage Application of PCT/IB2011/052941, filed 4 Jul. 2011, which claims benefit of Serial No. TO2010A000577, filed 5 Jul. 2010 in Italy and which applications are incorporated herein by reference. To the extent appropriate, a claim of priority is made to each of the above disclosed applications.

BACKGROUND OF THE INVENTION

The present invention in general falls within the field of devices for the immunologic detection of antigens.

More specifically, the invention relates to a planar support having an ultraflat surface useful for detecting antigens by label-free techniques, more particularly by AFM (Atomic Force Microscopy) imaging. The planar support of the invention is preferably provided in the form of an array of antibodies, such as for example a nanoarray or microarray of antibodies.

In the state of the art, the main analytical assay for detecting proteins of biological interest, such as for instance proteins useful as biomarkers, is represented by the ELISA (Enzyme-Linked ImmunoSorbent Assay) technique, which is known to be characterized by a detection limit of about 5 pg/ml and requires a minimum sample volume of about 50 μl.

Recently, the ELISA technique has been in part substituted with the protein microarray technique, which exhibits the advantage of being able to use smaller sample volumes and allowing for the simultaneous analysis of many analytes. Among which, antibody microarrays are known. A microarray of antibodies includes multiple antibody spots arranged in an ordered way, wherein each spot has a micrometric size and consists of multiple molecules of a single capture antibody directed against a predetermined individual antigen. With such a technique, the antigens are captured in a specific way by the antibodies and are mainly detected by fluorescent labeling techniques. The detection limit of the conventional microarrays is within the pM-fM range, the minimum volume of sample is in the order of picoliters, the size of the spots is typically comprised in the range of 100-300 μm in diameter and the quantity of the different antibodies/arrays is less than 500.

In this context, a further miniaturization would certainly be advantageous as it would allow to obtain a higher density in the array, use smaller volumes and reduce the amount of analyte. Several approaches were attempted to develop the so-called ultramicroarrays (Nettikadan S et al. Mol Cell Proteomics 2006, 5:895-901; Lee K B et al. Science 2002, 295: 1702-1705; Sekula S et al. Small 2008, 4:1785-1793; Zhang G J et al. J Nanosci Nanotechnol 2007, 7:410-417). Although technologies for printing a plurality of identical spots of nanometric size are already available (nanoprinting, nanolithography, nanodispensing), the issue of functionalizing each spot with a different antibody has not been completely solved yet (Wingren C et al. Drug Discov Today 2007, 12:813-819). Furthermore, the currently available scanners that are used for fluorescence detection are not capable of resolving spots of nanometric size (resolution≥1 μm) and the usefulness of the label-free techniques for detecting single molecules in disease proteomics has not been demonstrated yet.

In order to overcome the previously stated problems, particularly as regards the functionalizing of arrays with a plurality of different antibodies and the detection of nanometric spots, the present inventors concentrated their efforts on the creation of a planar support having an ultraflat surface, such that the support is suitable for manufacturing a nanoarray (or optionally a microarray) capable of being detected by AFM imaging. Indeed, such a technique allows for the detection of the formation of an Ab-Ag immunocomplex at concentrations that are lower than the fM range, without the need of using chemical labeling techniques such as for example the fluorescent labeling.

AFM imaging is known to allow for the detection of single molecules, under the proviso that the substrate is extremely smooth. For this reason, the substrate functionalizing method is particularly critical in AFM imaging.

Several functionalizing methods are known which allow the capture antibodies to maintain their own orientation and function. The most common approach consists in using antibody-binding proteins, such as protein A and protein G, which are able to specifically recognize the Fc region of antibodies. Even though such a method is simple and inexpensive, as it does not require the modification of the capture antibodies, it has the disadvantage of not being suitable to be used with the AFM imaging technique, because of the high molecular size of protein A and protein G. Other approaches described in the state of the art appear to be costly, both in terms of money and time, requiring the use of tagged recombinant antibodies (Steinhauer C et al. Proteomics 2006, 6:4227-4234; Torrance L et al. J Virol Methods 2006, 134: 164-170; Vallina-Garcia R et al. Biosens Bioelectron 2007, 23:210-217).

In the light of the above, a device for detecting antigens, such as for instance a nanoarray or microarray of capture antibodies, which is characterized by a high sensitivity, which allows for the use of very small sample volumes and relies on label-free detection techniques would be extremely desirable.

SUMMARY OF THE INVENTION

One object of the present invention is therefore to provide a device that is suitable for detecting antigens, such as for instance a nanoarray or microarray of capture antibodies, having the above-mentioned features.

Particular embodiments form the subject of the subordinate claims, the contents of which are understood to be an integral part of the description.

BRIEF DESCRIPTION OF THE DRAWINGS

Further features and advantages of the invention will appear from the detailed description that follows, carried out purely by way of a non-limiting example, with reference to the appended drawings, wherein.

DETAILED DESCRIPTION OF THE PREFERRED EMBODIMENTS

In order to overcome the problems of the prior art, particularly with reference to obtaining functionalized planar supports suitable for use in AFM imaging techniques, the present inventors provided a new functionalizing methodology, according to which a planar support made of a material characterized by having surface-exposed hydroxy groups (—OH), such as for example a glass, mica, or silicon substrate, is functionalized with a first monolayer of linking molecules, each having at least one amino group. The linking molecule is preferably bifunctional, that is capable of binding to one of the hydroxy groups exposed on the substrate surface at one of its own ends, whereas at the other end the linking molecule bears a free amino group, preferably a primary amino group. Non-limiting examples of such linking molecules are aminosilanes, such as 3-aminopropyltriethoxysilane (APTES) and 3-[2-(2-aminoethylamino)-ethylamino]-propyltrimethoxysilane (AEEA). APTES is preferred among them.

Figure 1:
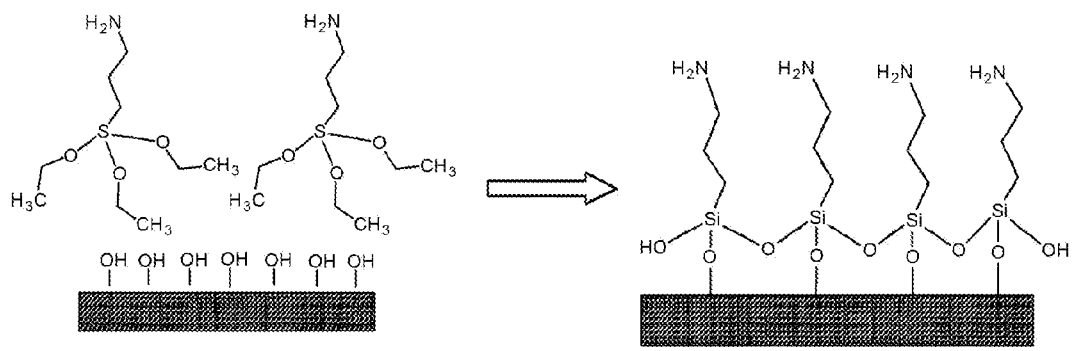
FIG. 1 is a scheme that represents the functionalizing of a Mica planar substrate with a monolayer of APTES molecules, according to an embodiment of the invention.

The formation of a monolayer of APTES molecules onto a mica substrate is represented in FIG. 1.

According to the functionalizing methodology set up by the inventors, the planar substrate is further functionalized with a second monolayer made of small peptides immobilized on the first monolayer by means of a peptide bond between the carboxyl terminal group of each peptide and the amino group of each linking molecule.

The peptides used for making the planar support of the invention have the general formula (I) that follows:

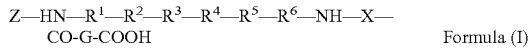

Formula (I)

wherein Z is a protecting group (such as for example acetyl, biotin, FMOC or the like), $R^1$ and $R^2$ are independently selected from the group consisting of basic and hydrophobic amino acids, $R^3$ is selected from the group consisting of basic and hydrophilic amino acids, $R^4$, $R^5$ and $R^6$ are independently selected from the group consisting of hydrophobic amino acids, X is a linear alkyl chain of 6 to 10 carbon atoms (preferably C6, C8 or C10) and G is glycine. All the bonds between the amino acids are carbamic bonds and preferably they involve the carboxyl and amino groups bound to the α carbon of each amino acid.

In the present description, the expression "basic amino acids" intends to include arginine, lysine and histidine; the expression "hydrophobic amino acids" intends to include glycine, alanine, valine, leucine, isoleucine, proline, methionine, phenylalanine, tryptophan; the expression "hydrophilic amino acids" intends to include serine, threonine, tyrosine, cysteine, asparagine, glutamine.

In a preferred embodiment of formula (I), $R^1$ is a hydrophobic amino acid, $R^2$ is a basic amino acid, $R^3$ is a hydrophilic amino acid, $R^4$, $R^5$ and $R^6$ are independently of each other hydrophobic amino acids.

In a particularly preferred embodiment, one single antibody-binding peptide is used for making the planar support, which most preferably has the following formula:

Formula (II)

wherein G is glycine, L is leucine, V is valine, T is threonine, R is arginine, P is proline, C8 is a linear alkyl chain of 8 carbon atoms and the amino terminal group is protected with an acetyl group.

The above-illustrated peptides of the general formula (I) are advantageously capable of affinity binding to the Fc moiety of antibodies and therefore are designated as "Antibody Binding Peptides" or "AbBPs".

The peptides of formula (I) per se fall within the scope of the present invention.

The planar support obtained by the above-illustrated functionalizing methodology exhibits advantageously an ultraflat surface (FIG. 2) which allows for the use thereof for manufacturing micro- and nano-arrays of capture antibodies suitable to be analyzed by AFM imaging.

Particularly, because of the use of the above-illustrated small peptides of the general formula (I), the capture antibodies that are immobilized onto the planar support maintain their own orientation and functionality; moreover, the so-functionalized planar support stays extremely smooth, due to the fact that the peptides of the general formula (I), being small in size, do not negatively affect the roughness of the support.

In this connection, it is known that the roughness of a support for AFM imaging must be lower than 1 nm. The present inventors performed specific roughness measurements and found that the roughness of a functionalized planar support as described above is within the subnanometric range; therefore, such a support is suitable for use in AFM imaging. More specifically, the inventors measured the following parameters:

$$R_a = \frac{1}{N}\sum_{j=1}^{N}|Z_j|$$

and $$R_q = \sqrt{\frac{\sum Z_i^2}{N}}$$

wherein $R_a$ is the arithmetic mean roughness and $R_q$ is the quadratic mean roughness.

The values obtained for $R_a$ and $R_q$ (see Examples 1 and 2) indicate that the planar support of the invention exhibits an extremely smooth surface, which may be defined as an "ultraflat" surface.

Thus, such a support is suitable to be used for manufacturing a device for detecting antigens in a sample, preferably a biological sample. To that end, one or more capture antibodies is/are placed onto the planar support by per se known techniques, which antibodies have the property of specifically and selectively binding the antigen(s) of interest, forming an Ab-Ag (antibody-antigen) complex.

Therefore, another aspect of the invention relates to a device for detecting antigens in a sample, preferably a biological sample, which comprises a planar support having an ultraflat surface, as previously described, on which one or more capture antibodies are immobilized.

According to a preferred embodiment, a plurality of different capture antibodies are immobilized on the planar support, each of which is placed on the support in the form of a spot, and wherein the totality of the spots forms an ordered arrangement or array. In this embodiment, the device of the invention is defined as a nanoarray (if the size of each individual spot is within the nanometric range) or a microarray (if the size of each individual spot is within the micrometric range). By way of example, by using the Piezoarray non-contact microarraying system (Perkin Elmer), the inventors obtained spot sizes in the range between 40 and 100 micron. By using a nanoprinting procedure, wherein the cantilever of the atomic force microscope is used directly for placing the antibodies onto the planar support, it is possible to obtain a decrease in the size of the spots to a nanometric scale. Alternatively, it is possible to use the antibody placement technique that is known as nanolithography Dip Pen or other technologies known in the art for the formation of nanoarrays.

As previously indicated, the formation of the Ab-Ag complex on the planar surface of the device of the invention, and thus the presence of the antigen(s) of interest in the tested sample, is preferably detected by AFM imaging, which is a per se known technique, the correct execution of which is perfectly within the ability of the person of ordinary skill in the art.

Therefore, the use of a device for detecting antigens as described above for the detection of at least one antigen in a sample, preferably a biological sample, by detecting the formation of a complex between the antigen (Ag) and its respective capture antibody (Ab), wherein the Ag-Ab complex is preferably detected by AFM imaging, is also within the scope of the present invention.

The detection device of the invention, which is analyzable by AFM, is suitable for use as an analytical assay in several applications for detecting multiple antigens in very small samples. In the medical research, the availability of antibody nanoarrays will have the effect of significantly speeding up the immunodiagnostics, as it will be possible to simultaneously analyze several significant diagnostic parameters. Also, the decrease in the minimum required volume of sample is very important for all the applications where minimal amounts of sample to be tested are available. One such example is the analysis of multiple tumor markers on very small amounts of biopsy material.

Furthermore, many important protein biomarkers, such as for instance PSA, HER-2, CRP, occur in blood at very low concentrations, between 10 and 100 pg/ml.

Another example is the analysis of cytokines and/or growth factors released by cell populations very poorly represented in peripheral blood or tissues. Modern technologies, such as fluorescence activated cell sorting (FACS) and laser capture microdissection (LCM), allow for the separation and collection of samples of purified cell populations and single cells. This makes the new technology set up by the present inventors particularly useful, the which allows to analyze proteins expressed by highly purified, yet very small samples.

Accordingly, the device of the invention allows for the detection of multiple biomarkers in parallel and at very low concentrations, even below the femtomolar range. This will have a very important effect on diagnostic applications, both from a technical and a commercial point of view. Technically, the device of the invention allows for the detection of single immunocomplexes. The sensitivity of such an instrument is therefore much higher than that of the ultramicroarrays detectable by fluorescence. Moreover, it must be pointed out that a label-free technique is faster, cheaper and it minimizes the false positives caused by fluorescence detection. Finally, the sample slides can be kept at room temperature under vacuum for an indefinite period of time without losing information. Commercially, the prospect of being able to simultaneously detect a high number of biomarkers below the femtomolar range, and thus with a considerable decrease in the minimum required volume of sample, makes the device of the invention usable in many different applications, such as for example the analysis of micro-samples, biopsies, neonatal samples, very poorly represented cell populations.

The following examples are provided by way of illustration and not limitation of the scope of the invention as defined in the appended claims.

EXAMPLES

1. Preparation of mica-APTES Ultraflat Substrates for AFM Imaging

Figure 2:
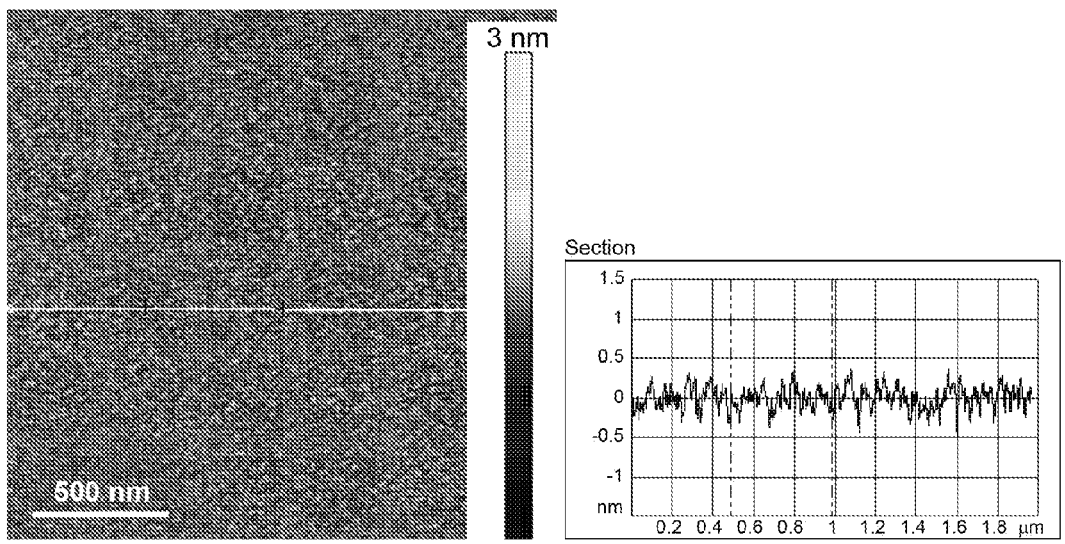
FIG. 2 is a topographic image obtained by Atomic Force Microscopy (AFM) of the surface of the mica planar substrate functionalized with the monolayer of APTES molecules obtained according to the scheme of FIG. 1.

An APTES-silanized mica surface having an extremely low roughness ($R_a$=0.109 nm; $R_q$=0.136 nm) was prepared, in the form of a solid planar substrate designed for the immobilization of antibodies (FIG. 2). Such an APTES-mica substrate has exposed amino groups ($-NH_2$). The APTES-mica substrate was prepared by placing a certain amount of mica that had just been cut into a glass vacuum desiccator that contained 50 µl of 98% APTES (Sigma) in an open Petri dish for 1 hour. The silanized substrate was then heated at 110° C.

2. Layering of a Monolayer of Small Peptides

The small antibody-binding peptides ("AbBPs") were synthesized by conventional synthesis techniques, the execution of which is well within the ability of the person of ordinary skill in the art.

Figure 3:
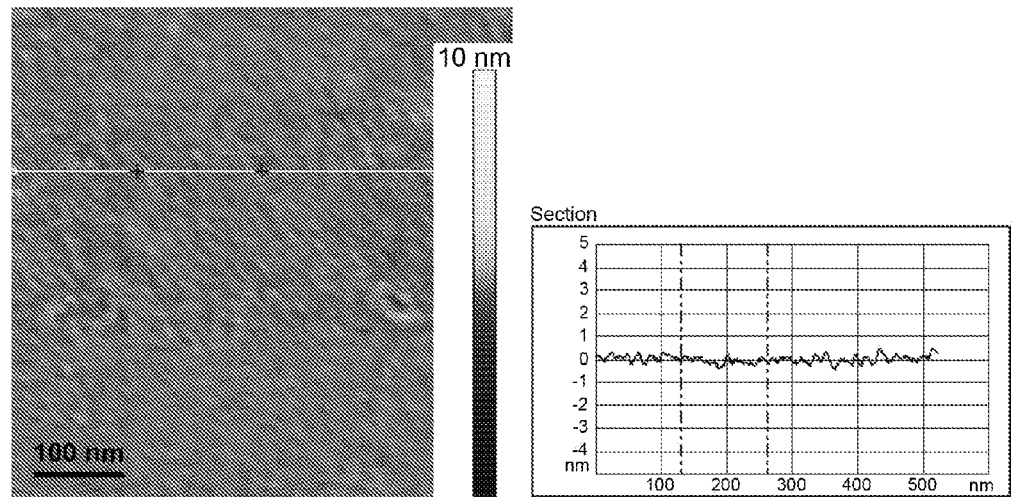
FIG. 3 is a topographic image obtained by Atomic Force Microscopy (AFM) of the surface of a planar support of the invention, obtained by the binding of specific Antibody Binding Peptides ("AbBPs") to the Aptes molecules of the functionalized planar substrate in FIG. 2.

In order to create the peptide monolayer on the APTES monolayer, 2 mg/ml of peptides AbBPs in DMF were treated with HATU and DIPEA to activate the carboxyl group. The solution was then placed overnight at room temperature onto the APTES-mica substrate obtained as described in Example 1. Thereby the peptide bonds between the surface-displayed amino groups and the peptide carboxyl groups were formed. The substrate was then washed with deionized water. A planar support having an ultraflat surface was thereby obtained, as illustrated in FIG. 3 ($R_a$=0.129 nm; $R_q$=0.166 nm).

3. Immobilization of Antibodies

Several concentrations of a commercial anti-IL10 (anti-interleukin 10) antibody were placed, in the form of spots, onto the planar support obtained as described in Examples 1 and 2, by using the Piezoarray non-contact microarraying system (Perkin Elmer), thereby obtaining an antibody array suitable to be used as a detection device for antigens in a sample.

Figure 4:
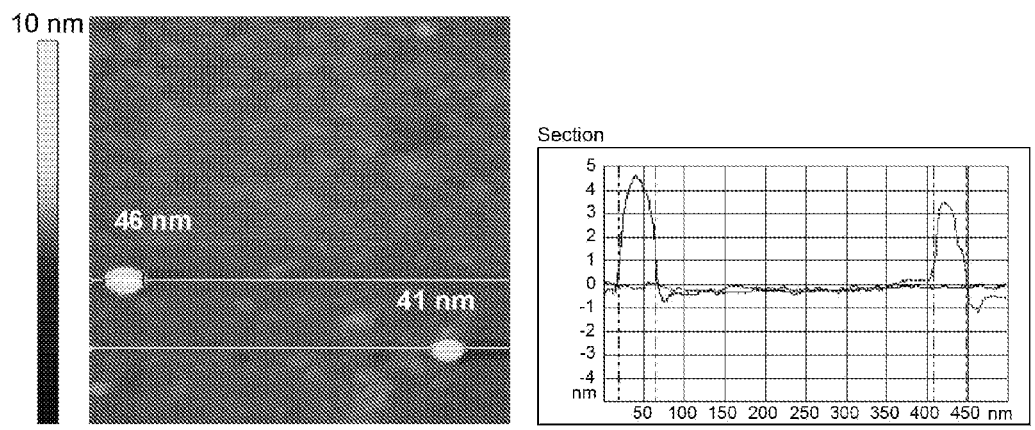
FIG. 4 is a topographic image obtained by Atomic Force Microscopy (AFM) of the surface of a device for detecting antigens according to the invention, wherein two antibodies immobilized on the planar support through binding with the "AbBP" peptide are visible, the said antibodies being visible in the form of a dot.

The antibodies were visualized on the surface of the planar support by the AFM imaging technique. Two antibodies are visible in FIG. 4, which are visualized as dots having a width of 30-40 nm and a height of 4-5 nm. The antibody concentration is 62.5 pg/ml.

4. Detection of the Formation of the Ag-Ab Complex

The antibody array obtained as described in the previous Examples was treated with a 1% amino acid mix in PBS in order to block the non-specific binding.

Figure 5A:
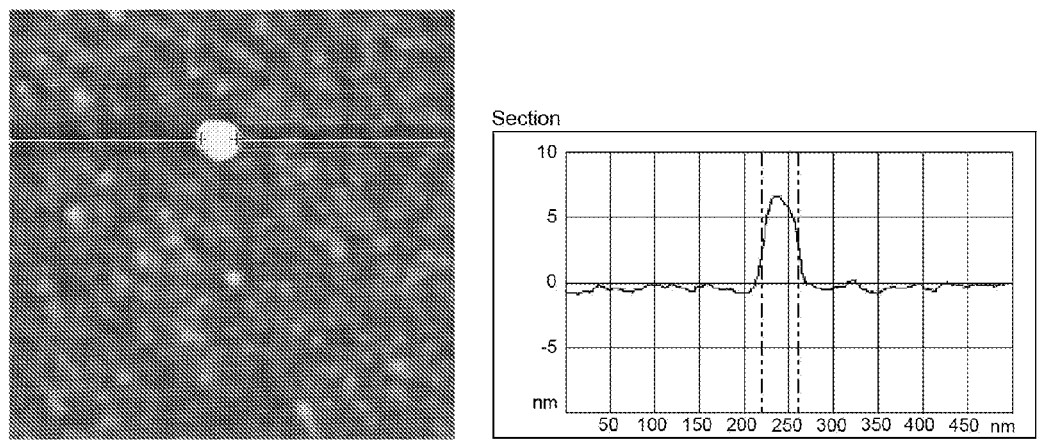
FIG. 5A is a topographic image obtained by Atomic Force Microscopy (AFM) of the surface of the device in FIG. 4, wherein an antigen-antibody immunocomplex is visible, the said complex being visible in the form of a dot.
Figure 5B:
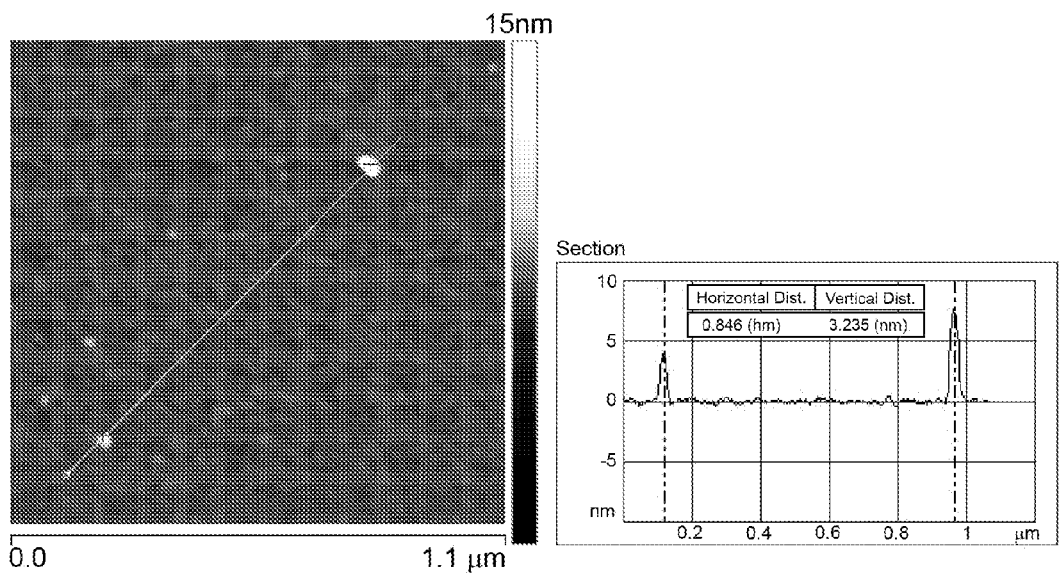
FIG. 5B shows the comparison of the height of an antibody dot with the height of the respective immunocomplex dot.

The antigen (Interleukin 10) was placed onto the array at several concentrations and the formation of the single immunocomplex was visualized by AFM. One immunocomplex is visible in FIG. 5A, which is visualized as a dot having a width of 40-50 nm and a height of 7-8 nm. The antibody concentration is 62.5 pg/ml, that of the antigen is 125 pg/ml. FIG. 5B shows a comparison between the heights of the dots from the antibody alone and the immunocomplex.

All the data obtained by AFM imaging were confirmed by fluorescence imaging.

The invention claimed is:

1. A device for detecting antigens in a sample, the device comprising:
    a planar support having a planar surface, comprising a planar substrate which is functionalized with:
    a first monolayer of linking molecules, each linking molecule including at least one amino group; and
    a second monolayer of peptides having the general formula (I):

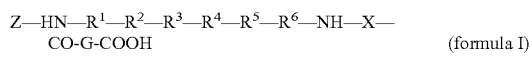

Z—HN—R$^1$—R$^2$—R$^3$—R$^4$—R$^5$—R$^6$—NH—X—CO-G-COOH    (formula I)

wherein Z is a protecting group, R$^1$ is proline, R$^2$ is arginine, R$^3$ is threonine, R$^4$ is valine, R$^5$ and R$^6$ are both leucine, and X is a linear alkyl chain of 8 carbon atoms and G is a glycine residue.

2. The device according to claim 1, wherein the planar substrate is made of a material having exposed hydroxyl groups.

3. The device according to claim 2, wherein the planar substrate is made of a material selected from mica, silicon and glass.

4. The device according to claim 1, wherein the device is a nanoarray or a microarray comprising a plurality of different capture antibodies.

5. A method of detecting an antigen in a sample, comprising:
    providing a sample suspected of containing said antigen;
    contacting the sample with a device according to claim 1;
    detecting formation of a complex between said antigen and said array of capture antibodies immobilized on said planar support.

6. The method according to claim 5, wherein the sample is a biological sample.

7. The method according to claim 5, wherein the formation of the antigen-antibody complex is detected by AFM (Atomic Force Microscopy) imaging.

* * * * *